United States Patent [19]

Peck

[11] Patent Number: 4,909,256

[45] Date of Patent: Mar. 20, 1990

[54] TRANSDERMAL VAPOR COLLECTION METHOD AND APPARATUS

[75] Inventor: Carl C. Peck, Rockville, Md.

[73] Assignee: The United States of America, as represented by the Secretary of the Army, Washington, D.C.

[21] Appl. No.: 121,306

[22] Filed: Nov. 16, 1987

Related U.S. Application Data

[63] Continuation-in-part of Ser. No. 660,778, Feb. 11, 1985, Pat. No. 4,706,676.

[51] Int. Cl.$^4$ .................................................. A61B 5/00
[52] U.S. Cl. ....................................... 128/632; 128/760
[58] Field of Search ................. 128/760, 767, 632, 637

[56] References Cited

U.S. PATENT DOCUMENTS

| | | | |
|---|---|---|---|
| 4,190,060 | 2/1980 | Greenleaf et al. | 128/760 |
| 4,280,505 | 7/1981 | Dali et al. | 128/635 |
| 4,329,999 | 5/1982 | Phillips | 128/760 |
| 4,396,017 | 8/1983 | Delpy et al. | 128/639 |
| 4,401,122 | 8/1983 | Clark, Jr. | 128/635 |
| 4,444,193 | 4/1984 | Fogt et al. | 128/632 |
| 4,457,748 | 7/1984 | Lattin et al. | 128/760 |
| 4,458,686 | 7/1984 | Clark, Jr. | 128/635 |
| 4,595,011 | 6/1986 | Phillips | 128/635 |
| 4,624,261 | 11/1986 | Holscher | 128/670 |

OTHER PUBLICATIONS

Peck et al., "A Non-Invasive Transepidermal Toxicological Monitoring Device", Pittsburgh Conference and Exposition on Analytical Chemistry and Applied Spectroscopy, Mar. 9, 1982, Meeting Abstracts Book, p. 366.

Bumgardner et al., "Gas Flux Through Human Skin: Effect of Temperature, Stripping, and Inspired Tension", Reprint 0161-7567/85, The American Physiological Society, pp. 1536-1545, 1985.

Susten et al., "In Vivo Percutaneous Absorption Studies of Volatile Solvents in Hairless Mice. I. Description of a Skin-Depot", Reprint 0260-437X/86/010043-04, John Wiley & Sons, Ltd., pp. 43-46, 1986.

Primary Examiner—Max Hindenburg
Assistant Examiner—Randy Shay
Attorney, Agent, or Firm—Werten F. W. Bellamy; Anthony T. Lane

[57] ABSTRACT

A method for the non-invasive, continuous collection of substances which transdermally migrate to and vaporize at the surface of the skin of a subject comprises providing a binding reservoir material juxtaposed at the surface of the skin of a subject, and continuously maintaining the binding reservoir material in a substantially airtight relation with the skin surface over an entire collection period. The apparatus comprises a binding reservoir material and means for continuously maintaining the binding reservoir material juxtaposed at the skin surface of the subject in a substantially airtight relation wiht the skin surface.

17 Claims, 1 Drawing Sheet

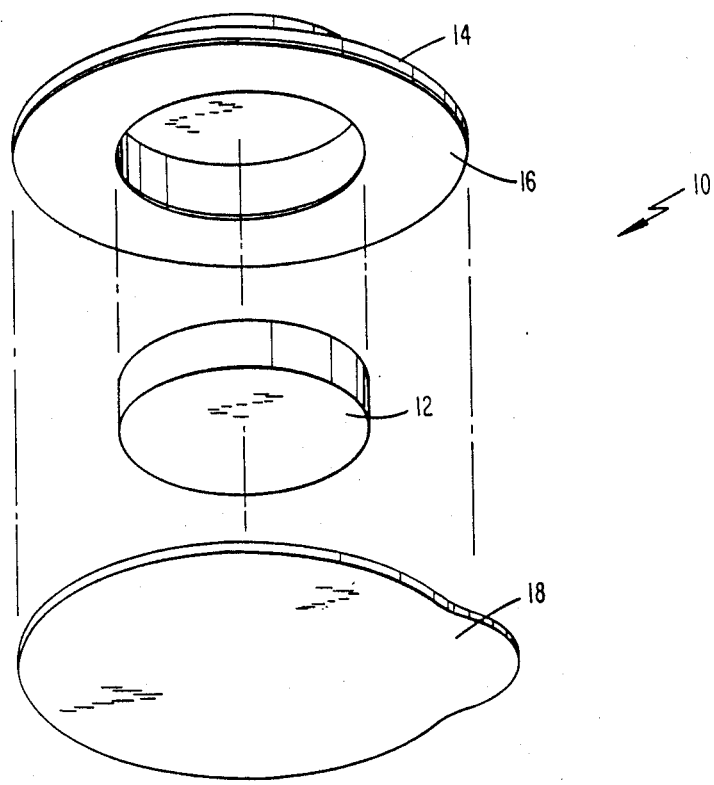

TRANSDERMAL VAPOR COLLECTION METHOD AND APPARATUS

RELATED APPLICATION

This application is a continuation-in-part of U.S. patent application Ser. No. 660,778 filed Feb. 11, 1985 now U.S. Pat. No. 4,706,676.

FIELD OF THE INVENTION

The present invention relates to a method and apparatus for the non-invasive, continuous collection of substances which transdermally migrate to and vaporize at the surface of the skin of a subject. More particularly, the present invention relates to a transdermal vapor collection method and apparatus which employ a binding reservoir material for collecting the vapors and preventing their escape into the environment or their migration back into the skin.

BACKGROUND OF THE INVENTION

Many chemicals enter the bodies of animals, both human and nonhuman, in various manners, for example, across skin, by inhalation, by oral ingestion and by direct injection through the skin into subcutaneous tissues and muscle or directly into blood vessels. These chemicals are distributed in the body via blood circulation. Owing to concentration gradients, a small portion of the circulating chemicals, or one or more of their metabolites, may migrate outwardly from skin capillaries, across the epidermis and stratum corneum to the skin surface. If the thus migrated chemicals or metabolites are vaporous at the skin surface temperature, they will escape from the skin surface into the adjacent environment. Additionally, gases such as oxygen and carbon dioxide in capillary blood also diffuse to the skin surface and escape.

Various methods and apparatuses are known in the art for assessing human exposure to chemicals by monitoring and/or collecting substances which migrate to a subject's skin surface. For example, Applicant's copending application Ser. No. 660,778 discloses a dermal substance collection device for the transdermal collection of non-volatile chemicals. However, the device disclosed therein includes a fluid conduit between the skin surface and the binding component, a feature which is counterproductive for the collection of chemicals in the vapor state. Similarly, the Phillips U.S. Pat. No. 4,595,011 discloses a transdermal dosimeter for monitoring exposure to chemical agents which includes a fluid phase serving as a dermal contact bridge.

Peck et al in "A Non-Invasive Transepidermal Toxicological Monitoring Device", Pittsburgh Conference and Exposition on Analytical Chemistry and Applied Spectroscopy", Mar. 9, 1982, *Meeting Abstracts Book*, page 366, disclose a transepidermal device including an adhesive plastic chamber containing sodium chloride-impregnated absorbent pads and an activated charcoal impregnated disk for capturing a xeobiotic to prevent back transfer from the collection device into the body. Similarly, the Phillips U.S. Pat. No. 4,329,999 discloses a patch including sodium chloride-impregnated absorbent pads for absorbing sweat from the skin surface of a patient. Sodium chloride interferes with the collection of chemicals which are in the vapor state.

The Delpy et al U.S. Pat. No. 4,396,017 discloses a transcutaneous gas sensor including a sensing electrode which is applied to the boyy surface of a patient with an electrolyte layer between the electrode and the patient's body. Gas which has diffused through the patient's body from his blood to the body surface results in an electrochemical reaction at the exposed surface of the electrode. Similarly, the Dali et al U.S. Pat. No. 4,280,505 discloses a transcutanoous gas sensor probe for the measurement of trancutaneousggases emitted through the skin of a living body.

Additional methods are also known for determining the presence of various chemicals in the body. For example, tissue biopsies and blood sampling are used but are disadvantageous owing to their invasive character. Other methods such as collection of urine or saliva are disadvantageous owing to the difficulty of obtaining continuous monitoring. A need exists for a method and apparatus for the non-invasive and continuous collection of substances which transdermally migrate to and vaporize at the surface of the skin of a subject.

SUMMARY OF THE INVENTION

Accordingly, it is an object of the present invention to provide a method for the non-invasive and continuous collection of substances which transdermally migrate to and vaporize at the surface of the skin of a subject. It is a related object to provide an apparatus for the non-invasive and continuous collection of substances which transdermally migrate to and vaporize at the surface o the skin of a subject. It is a further object of the invention to provide a method which facilitates the subsequent analysis of collected vapors and assessment of body conditions and exposures.

These and additional objects are provided by the method and apparatus of the present invention. More specifically, the present invention relates to a method for the non-invasive, continuous collection of substances which transdermally migrate to and vaporize at the surface of the skin of a subject. The method comprises providing a binding reservoir material juxtaposed at the surface of the skin of the subject, and continuously maintaining the binding reservoir in a substantially airtight relation with the skin surface over an entire collection period. The substances which migrate to and vaporize at the skin surface are collected in the binding reservoir and are prevented from escaping into the environment or migrating back into the skin. The present invention further relates to an apparatus for the non-invasive, continuous collection of substances which transdermally migrate to and vaporize at the surface of the skin of a subject. The apparatus comprises a binding reservoir material, and means for continuously maintaining the binding reservoir material juxtaposed at the surface of the skin of a subject in a substantially airtight relation with the skin surface over an entire collection period. Thus, when substances migrate to and vaporize at the skin surface, they are collected in the binding reservoir and are prevented from escaping into the environment or from migration back into the skin.

Additional objects and advantages of the method and apparatus of the present invention will become more apparent in view of the following detailed description.

DESCRIPTION OF THE DRAWINGS

The following detailed description will be more fully understood in view of the drawing in which:

FIG. 1 sets forth an enlarged cross-sectional view of an embodiment of the apparatus according to the present invention; and FIG. 2 sets forth an exploded perspective view of the apparatus according to the present invention as set forth in FIG. 1.

DETAILED DESCRIPTION

The present invention comprises a method and apparatus for he non-invasive and continuous collection of substances which transdermally migrate to and vaporize at the surface of the skin of a subject. The method and apparatus are useful for collecting vapors from the skin surface of both human and nonhuman animals. The method and apparatus are useful for various applications including, for example, the monitoring of exposure to hazardous chemicals such as industrial solvents, pesticides, and various other chemical agents, monitoring exposure to volatile drugs of abuse such as ethanol, and monitoring exposure to environmental volatile toxic chemicals.

The method of tee present invention comprises providing a binding reservoir material juxtaposed at the surface of the skin of a subject, which binding reservoir material is capable of collecting and retaining substances in the vapor phase. Charcoal material is a highly advantageous binding reservoir material for collecting substances in the vapor phase. Additionally, when the charcoal is in a dry condition, the vapor collection is unimpeded by the presence of a fluid barrier medium interposed between the skin surface and the collection device. A preferred charcoal material is activated charcoal or activated carbon which is obtained by the destructive distillation of various carbonaceous materials followed by an "activation" process which usually comprises heating the resultant material at a high temperature, for example, 800° to 900° C., in the presence of steam or carbon dioxide to provide a porous internal structure.

Alternatively, the binding reservoir material may comprise other materials which are capable of collecting and retaining substances in the vapo- phase. For example, the binding reservoir material may comprise molecular sive materials, namely alkaline metal aluminosilicates similar to natural clays and feldspars, which comprise networks of empty pores and cavities, generally of uniform size. Molecular sieves are particularly suitable for collecting alcohols which migrate to and vaporize at the skin surface. Silica gels are also suitable for use as the binding reservoir material as are silica gels which have been modified with aromatic or aliphatic group-containing salines. Activated aluminas, ion exchange resins , for example , cholestyramine, and chelating agents are also suitable for use as the binding reservoir material. The binding reservoir material should not include a liquid component since liquids generally inhibit the collection of vapor substances. Thus, the binding reservoir material should be in solid or semi-solid form.

In a preferred embodiment, the binding reservoir material is impregnated on a carrier member. The carrier member may be formed of any number of substantially inert materials, for example, cloth or a perforated or porous plastic material. It is preferred that the carrier member is flexible in order to conform to the skin surface. A preferred carrier material comprises the polytetrafluoroethylene materials sold under the trade name Teflon ®.

The method according to the present invention further comprises the step of continuously maintaining the binding reservoir material in a substantially airtight relation with the skin surface over the collection period. The airtight relation of the binding reservoir material with the skin surface serves two purposes. First, the airtight relation insures collection of substances emanating only from the skin surface and prevents contamination of the binding reservoir material by environmental vapors. Second, the airtight relation establishes total skin-surface occlusion which results in hydration of the stratum corneum. Hydration of the stratum corneum enhances the transdermal migration of various substances since many chemicals permeate the hydrated stratum corneum faster than they permeate the dry stratum corneum.

In a preferred embodiment of the present invention, the binding reservoir material is maintained in a substantially airtight juxtaposed relation with the skin surface by means of an airtight, flexible, adhesive cover means. The cover may be formed, for example, from a metal foil or from an impermeable plastic film material. It is preferred that at least a portion of the cover means includes an adhesive coating for adhering the cover means to the skin surface in an airtight manner.

FIG. 1 discloses an enlarged cross-sectional view of an embodiment of the apparatus 10 according to the present invention. The apparatus includes a binding reservoir material 12 and cover means 14 for maintaining the binding reservoir material juxtaposed at the surface of the skin of a subject in a substantially airtight relation with the skin surface. As set forth in FIG. 1, surfaces 16 of the cover means are provided with an adhesive coating for adhering the cover means to the skin surface of the subject. The transdermal collection apparatus may further include a removable impermeable cover means 18 which covers the portion of the binding reservoir material adapted for juxtaposition at the skin surface prior to use of the apparatus. The cover prevents contamination of the binding reservoir material prior to use of the apparatus and is adapted to be removed from the apparatus prior to use. Materials suitable for use as the removable cover include metal foils and impermeable plastic films. FIG. 2 sets forth an exploded perspective view of the transdermal vapor collection apparatus of the present invention.

By juxtaposition of the binding reservoir at the skin surface with an occlusive, airtight cover means, body chemicals which have transdermally migrated to and vaporized at the skin surface are collected. The amount of collected chemicals is proportional to the time-integrated blood concentration of the subject chemical. The binding reservoir material binds the vaporous substances and prevents them from escaping into the environment or from migrating back into the skin.

In a preferred embodiment of the method of the present invention, the skin surface on which the binding reservoir material i to be positioned is first cleaned prior to providing the binding reservoir material juxtaposed thereto. For example, the skin surface may be cleansed and defeated by gently scrubbing with isopropyl alcohol or the like. The binding reservoir material may be juxtaposed at the skin surface of the subject in a substantially airtight relation with the skin surface for a period of time which is dependent on the target vapor substance which is to be collected. For example, the binding reservoir may be maintained at the skin surface for a time period ranging from several minutes to several days. Once the collection period is complete, the binding reservoir material may be removed from the skin surface for further analysis. For example, when the binding reservoir material comprises a charcoal impregnated carrier, it may be immersed in a predetermined amount of an organic solvent in order to transfer the collected vapors from the binding reservoir material to the organic solvent. One suitable organic solvent comprises hexane. The solvent may then be subjected to analysis, for example, by gas chromatography, in order to determine the amount and character of the collected substance.

The method and apparatus of the invention are illustrated by the following example.

EXAMPLE

This example of the method and apparatus for transdermal vapor collection according to the present invention involves the collection of isoflurane through the skin of a living "fuzzy" rat. Transdermal vapor collection devices including an activated charcoal binding reservoir material are placed on the back or the abomen of the rat prior to intraveneous administration of isoflurane. The intraveneous infusion of isoflurane is in the form of one or more bolus injections or may be maintained as a constant infusion for a prescribed time period. Generally, the transdermal vapor collection devices may be removed at various times during and following the end of the infusion period. Once removed, the binding reservoir component of the device is placed in a small volume of pesticide grade hexane for extraction of the isoflurane and subsequent quantitative analysis by gas chromatography. Blood samples drawn during and after the infusions are also analyzed by gas chromatography to determine the whole blood isoflurane concentrations resulting from isoflurane infusions. The amount of isoflurane in the transdermal vapor collection device may be related to the concentration of isoflurane in the blood by the following relationship:

$$TCD(amt) = K_p \times AUC \times A$$

where, TCD(amt) is the amount of isoflurane in the transdermal vapor collection device in micrograms, $K_p$ is an "apparent" permeability coefficient in cm/min, AUC is the area under the isoflurane blood concentration-time curve in mcg-min/ml, and A is the surface area of the transdermal vapor collection device in $cm^2$.

In a representative experiment, the infusion pump was set to deliver 12.5 mcl/min of a solution containing 120 mg/ml of isoflurane for 98.5 minutes (total dose of infused isoflurane was 147.4 mg) into a "fuzzy" rat weighing 364 grams. The average amount of isoflurane collected in four transdermal vapor collection devices removed from the rat's back at the end of the infusion period, extracted in hexane and assayed by gas chromatography, was 0.8 mcg (+/−0.2 mcg, standard deviation). Since the area under the isoflurane blood concentration-time curve from the beginning of infusion to the time of TCD removal was 2364 mcg-min/ml, and the surface area of the TCD was 0.95 $cm^2$, the calculated permeability coefficient according to the above relationship was $3.5 \times 10^{-4} +/- 8.0 \times 10^{-5}$ cm/min (mean +/−standard deviation, n=4).

Thus, the method and apparatus of the present invention provide non-invasive and continuous collection of substances which transdermally migrate to and vaporize at the skin surface of a subject in a simple manner. Moreover, the method and apparatus of the present invention are readily adaptable to subsequent methods for measuring and characterizing collected substances. Th preceding examples of materials suitable for use in connection with the method and apparatus of the present invention are set forth to illustrate specific embodiments of the invention and are not intended to limit the scope of the methods and apparatus of the present invention. Additional embodiments and advantages within the scope of the claimed invention will be apparent to one of ordinary skill in the art.

What is claimed is:

1. A method for the non-invasive continuous collection of substances which transdermally migrate to and vaporize at tee surface of the skin of a subject, comprising (a) providing a binding reservoir material juxtaposed at the surface of the skin of the subject, (b) continuously maintaining the binding reservoir material in a substantially airtight relation with the skin surface over an entire collection period, whereby substances which have migrated to and vaporized at the skin surface are collected in the binding reservoir material and are prevented from escaping into the environment or migrating back into the skin, (c) removing the binding reservoir material from the skin surface, and (d) immersing the binding reservoir of step (c) in a predetermined quantity of organic solvent, whereby the collected vapors are transferred from the binding reservoir material to the organic solvent.

2. A method as defined by claim 1, wherein said providing step includes providing said binding reservoir material in a solid or semi-solid form.

3. A method as defined by claim 1, wherein said providing step includes providing a binding reservoir material selected from the group consisting of charcoal, molecular sieve materials, silica gels, silica gels modified with aromatic or aliphatic group-containing silanes, ion exchange resins and chelating agents.

4. A method as defined by claim 1, wherein said providing step includes providing said binding reservoir material impregnated on an inert carrier member.

5. A method as defined by claim 4, wherein said providing step includes providing said binding reservoir material impregnated on a carrier made of polytetrafluoroethylene material.

6. A method as defined by claim 1, wherein the binding reservoir material is maintained in a substantially airtight relation with the skin surface by an airtight, flexible, adhesive cover means.

7. A method as defined by claim 6, wherein said maintaining step includes employing cover means made of a material selected from metal foils and impermeable plastic films, at least a portion of which includes an adhesive coating to maintain said binding reservoir material in substantially airtight relation with the skin surface.

8. A method as defined by claim 1, wherein the skin surface is cleaned prior to providing the binding reservoir material juxtaposed thereto.

9. An apparatus for the non-invasive, continuous collection of substances which transdermally migrate to and vaporize at the surface of the skin of a subject, comprising (a) a fluid-free binding reservoir material, and (b) means for continuously maintaining the fluid-free binding reservoir material juxtaposed at the surface of the skin of the subject in a substantially airtight relation with the skin surface over an entire collection period, said airtight relation being sufficient to ensure that when substances migrate to and vaporize at the skin surface they are collected in the fluid-free binding reservoir material and are prevented from escaping into the environment or migrating back into the skin.

10. An apparatus as defined by claim 9, wherein the binding reservoir material is in a solid or semi-solid form.

11. An apparatus as defined in claim 9, wherein the binding reservoir material is selected from the group consisting of charcoal, molecular sieve materials, silica gels, silica gels modified with aromatic or aliphatic group-containing silanes, ion exchange resins and chelating agents.

12. An apparatus as defined by claim 9, wherein the binding reservoir material is impregnated on an inert carrier member.

13. An apparatus as defined by claim 12, wherein the carrier member is formed of a polytetrafluoroethylene material.

14. An apparatus as defined by claim 9, wherein the means for continuously maintaining the binding reservoir material in a substantially airtight relation with the skin surface comprises an airtight, flexible, adhesive cover means.

15. An apparatus as defined by claim 14, wherein the cover means is formed from a material selected from metal foils and impermeable plastic films, and at least a portion of the cover means includes an adhesive coating for adhering to the skin surface.

16. An apparatus as defined by claim 9, further including a removable impermeable cover means covering the portion of the binding reservoir material adapted for juxtaposition at the skin surface, which cover is adapted to be removed from the apparatus prior to use for the collection of transdermally migrating vapors.

17. An apparatus as defined by claim 16, wherein the removable cover means is formed from a material selected from metal foils and impermeable plastic films.

* * * * *